(12) United States Patent
Yoshida et al.

(10) Patent No.: US 7,351,316 B2
(45) Date of Patent: Apr. 1, 2008

(54) WATER ELECTROLYSIS METHOD AND DEVICE FOR DETERMINATION OF HYDROGEN AND OXYGEN STABLE ISOTOPIC COMPOSITION

(75) Inventors: Naohiro Yoshida, Meguro-ku (JP); Osamu Abe, Moriyama-ku (JP); Ryu Uemura, Kita-ku (JP); Hiroshi Watanabe, Shinjuku-ku (JP)

(73) Assignees: Japan Science and Technology Agency, Kawaguchi-shi, Saitama (JP); Tokyo Institute of Technology, Meguro-ku, Tokyo (JP)

( * ) Notice: Subject to any disclaimer, the term of this patent is extended or adjusted under 35 U.S.C. 154(b) by 326 days.

(21) Appl. No.: 10/538,290

(22) PCT Filed: Dec. 12, 2003

(86) PCT No.: PCT/JP03/15999

§ 371 (c)(1),
(2), (4) Date: Jun. 10, 2005

(87) PCT Pub. No.: WO2004/055241

PCT Pub. Date: Jul. 1, 2004

(65) Prior Publication Data

US 2006/0076246 A1    Apr. 13, 2006

(30) Foreign Application Priority Data

Dec. 13, 2002   (JP) .............................. 2002-361726

(51) Int. Cl.
*C25B 9/10* (2006.01)
(52) U.S. Cl. ...................... 204/252; 204/257; 204/258; 205/627; 205/628; 205/629; 205/633; 205/639; 205/630; 205/631

(58) Field of Classification Search ................ 204/252, 204/258, 257; 205/627, 628, 629, 633, 634, 205/637, 638, 639, 630, 631
See application file for complete search history.

(56) References Cited

U.S. PATENT DOCUMENTS 3,981,976 A    9/1976  Stevens
(Continued)

FOREIGN PATENT DOCUMENTS

EP    0 806 498 A1    11/1997
(Continued)

OTHER PUBLICATIONS

Maruzen, *New Experimental Chemistry Series 10, Space and Geo Chemistry*, 1976, pp. 485-491.
(Continued)

*Primary Examiner*—Bruce F. Bell
(74) *Attorney, Agent, or Firm*—Squire, Sanders & Dempsey L.L.P.

(57) ABSTRACT

Water electrolysis device determining stable isotopic composition of water and a water electrolysis method for stable isotopic composition of water capable of analyzing many samples easily, safely and at low cost in very short time, and rapidly analyzing $^{17}O$ are provided. The water electrolysis device performing mass spectrometry of hydrogen or oxygen stable isotopic composition includes a proton exchange membrane of fluorocarbon polymer plated non-electrolytically with platinum, iridium, rhodium or iridium-rhodium alloy, and a cathode and an anode of porous titanium plated with platinum and sandwiching the proton exchange membrane, wherein water electrolyzes by introduction into the anode side chamber and supplying DC current between the anode and the cathode, and oxygen gas generated at the anode and hydrogen gas generated at the cathode respectively flows into an isotope ratio mass spectrometer. Water electrolysis method for stable isotopic composition of water using the water electrolysis device is also provided.

7 Claims, 7 Drawing Sheets

U.S. PATENT DOCUMENTS 4,050,995 A * 9/1977 Bredeweg .................. 205/788
6,297,501 B1 * 10/2001 Merren ....................... 250/296
2002/0054832 A1 * 5/2002 Amirav et al. ................ 422/89

FOREIGN PATENT DOCUMENTS

| JP | 8-26703 | 1/1996 |
|---|---|---|
| JP | 3048146 | 3/2000 |
| JP | 2000-243344 | 9/2000 |

OTHER PUBLICATIONS

Meijer et al, "The use of electrolysis for accurate delta7 0 and delta18 0 isotope measurements in water", Isotopes Environ. Health Stud., vol. 34, 1998, pp. 349-369, XP009037797.

* cited by examiner

WATER ELECTROLYSIS METHOD AND DEVICE FOR DETERMINATION OF HYDROGEN AND OXYGEN STABLE ISOTOPIC COMPOSITION

CROSS-REFERENCE TO RELATED APPLICATIONS

This application is a U.S. National Stage application claiming the benefit of prior filed International Application Number PCT/JP2003/015999, filed Dec. 12, 2003, in which the International Application claims a priority date of Dec. 13, 2002 based on prior filed Japanese Patent Application Number 2002-361726, the entire contents of which are incorporated herein by reference.

TECHNICAL FIELD

The present invention relates to a water electrolysis method for the determination of stable isotopic composition of water and a related analytical method by isotope ratio mass spectrometry. More specifically, the present invention relates to a water electrolysis method for the determination of hydrogen and oxygen stable isotopic composition of water by isotope ratio mass spectrometer.

BACKGROUND ART

In recent years, researches for deducing past variation or presuming future change of the global environment by the determination of hydrogen and oxygen stable isotopes of water such as rainwater, soil water, or polar ice core are actively conducted, and isotope ratio mass spectrometers for implementing this are also under development (See, for example, Patent document 1). For example, meteoric water in the subtropical or temperate regions show characteristic seasonal variations in their isotopic composition, which can provide important information as suggesting that the source of the meteoric water and/or the temperature at which water vapor are condensed change seasonally. This also provides an index for tracking changes in flow condition of groundwater when an assessment of construction project is conducted in association with huge undertaking.

Stable isotopic composition of water is usually analyzed in a separate manner such that a hydrogen isotope is determined as a form of hydrogen gas and an oxygen isotope is determined principally as a form of carbon dioxide gas or exceptionally as a form of oxygen gas because water vapor is an adsorptive gas having high affinity to metals, which will reduce the precision of accuracy for the determination significantly. To determine hydrogen stable isotopic composition of water using isotope ratio mass spectrometer (hereafter IRMS), a reduction method, an equilibrium method, and the like have been used. The reduction method is performed by reacting water molecules with metals such as uranium or zinc at the high temperature in vacuum to generate hydrogen gases. These hydrogen gases introduce directly to the IRMS (See, for example, non-patent document 1). On the other hand, the equilibrium method is performed by equilibrating water with arbitrary hydrogen gas at a constant temperature under the presence of platinum catalyst. This reaction is represented in Chemical formula 1

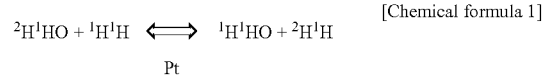

[Chemical formula 1]

The reduction method described in the non-patent document 1, however, entailed the problems that a vacuum device is required, the platinum catalyst used for the reaction is expensive, and it is difficult to prevent the metal surface from getting oxidized. Also the equilibrium method described in the non-patent document 1 had a problem that it requires 1 hour or longer time to reach the equilibration for hydrogen isotope between water and hydrogen gas as represented in Chemical formula 1, and the automated equipment for this reaction is expensive.

On the other hand, to determine oxygen stable isotopic composition of water, an equilibrium method and an oxidation method were performed conventionally. The equilibrium method is performed by equilibrating water with arbitrary carbon dioxide gas at a constant temperature to obtain the oxygen isotope equilibrium between them, as represented by Chemical formula 2 (See, for example, non-patent document 2). The oxidation method is performed by reacting water with fluorides such as bromine pentafluoride to extract oxygen gas (See, for example, non-patent document 2).

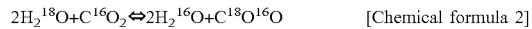

[Chemical formula 2]

The conventional equilibrium method described in the non-patent document 2, had the problems that it requires 10 hour or longer time to reach the isotopic equilibration for oxygen isotope between water and carbon dioxide as represented in Chemical formula 2. It is impossible to analyze $^{17}O$ using a conventional IRMS which has relatively low resolution for separating the small difference of masses of isotopic isomer between $^{12}C^{17}O^{16}O$ and $^{13}C^{16}O^{16}O$. The automated equipment for this reaction is expensive. The conventional oxidation method described in the non-patent document 2 had the problems that a vacuum device is required and handling of bromine pentafluoride and the like is difficult and dangerous.

There is an alternative method to determine hydrogen and oxygen isotopic composition, which is a specific method using the tunable diode-laser spectroscopy. Since it is free from the constraint that those having equivalent masses cannot be determined as is the case of the mass spectrometry, it is possible to determine $^{17}O$. However, laser spectroscopy for the determination of stale isotopic composition of water is a very specialized analytical method and is still inferior in accuracy to conventional isotope ratio mass spectrometry at this time.

For addressing these problems, another method attempts to determine the contents $^{17}O$ by extracting oxygen gas by electrolysis in a single electrolytic chamber which contains platinum serving as an anode and an oxygen-free carbon electrode serving as a cathode in an copper sulfate solution (See, for example, non-patent document 3).

According to the method described in the non-patent document 3, however, it is necessary to add an electrolyte, and addition of electrolyte may cause the analytical error in isotope ratio mass spectrometry or cause the failure of the IRMS. Furthermore, in the above method, it is possible to extract only oxygen but not a hydrogen isotope. Additionally, it takes 40 minutes to extract enough amount of oxygen gas for use in mass spectrometry.

In addition, conventionally, since oxygen gas and hydrogen gas can be extracted only as gas mixture from same sample water, it is necessary to provide an analytical procedure to separate oxygen gas and hydrogen gas from obtained mixture of oxygen gas and hydrogen gas in order to determine oxygen stable isotopic composition and/or hydrogen stable isotopic composition.

The following are prior art references related to the present invention.

Patent document 1: Japanese Patent Gazette No. 3048146

Non-patent document 1: New Experimental Chemistry Series 10, Space and Geo Chemistry, 1976, MARUZEN, p. 485.

Non-patent document 2: New Experimental Chemistry Series 10, Space and Geo Chemistry, 1976, MARUZEN, p. 486-p. 491.

Non-patent document 3: H. A J. MEIJER and W. J. LI, THE USE OF ELECTROLYSIS FOR ACCURATE $\delta^{17}O$ AND $\delta^{18}O$ ISOTOPE MEASUREMENTS IN WATER, "Isotopes Environ. Health Stud.," (India), 1998, Vol. 34, p. 349-369.

DISCLOSURE OF INVENTION

The present invention was devised in consideration of the above problems, and it is an object of the present invention to provide a water electrolysis method for stable isotopic composition of water and a related analytical method by isotope ratio mass spectrometry, which is capable of analyzing a number of samples with ease, with safety, and at low cost in a very short time, as well as enabling rapid analysis of $^{17}O$. Inventors of the present invention made strenuous efforts to achieve the above object, and, after a process of trial and error, finally accomplished the present invention.

In order to achieve the above object, the present invention provides a water electrolysis device for the determination of stable isotopic composition of water and a related analytical method using isotope ratio mass spectrometry of hydrogen stable isotopic composition or oxygen stable isotopic composition. The water electrolysis device (hereafter WED) includes a proton exchange membrane (hereafter PEM) which is made of fluorocarbon polymer plated non-electrolytically with platinum, iridium or iridium-rhodium alloy, and which is sandwiched between a cathode and an anode both made of porous titanium plated with platinum. Water is introduced to the anode side and electrolyzed by supplying a DC current between the anode and the cathode, and oxygen and hydrogen gases generated at the anode and cathode side respectively are allowed to flow into the IRMS.

Preferably, WED for the determination of stable isotopic composition of water according to the present invention has means for feeding nitrogen gas to each of pathways which leads the oxygen and hydrogen gases generated at the anode and cathode side respectively to the IRMS, whereby atmospheric oxygen and remaining water in each pathway can be removed by this nitrogen gas.

Still preferably, WED for the determination of stable isotopic composition of water according to the present invention has a double-tube dehumidifying part in each pathway to remove water vapor from oxygen and hydrogen gases generated at anode and cathode side respectively. The double-tube dehumidifying part has an inner tube wall formed of a fluorocarbon polymer membrane. By letting air having dried by silica gel flow between an inner tube and an outer tube, only such water vapor that prevents mass spectrometric determination is removed from the oxygen gas or hydrogen gas flown into the inner tube. Thus, the gases can be dehumidified before being introduced into the IRMS.

The analytical method to determine hydrogen and oxygen stable isotopic composition of water according to the present invention is characterized by: (1) electrolyzing sample water without adding any electrolyte; (2) separately extracting hydrogen gas and oxygen gas to introduce them into an IRMS; and (3) conducting the analysis for the determination of hydrogen and oxygen stable isotopic composition contained in the sample water.

Furthermore, the mass spectrometric determination for stable isotopic composition of water according to the present invention is characterized by, with regard to the oxygen isotope $^{17}O$ contained in water, electrolyzing sample water without adding any electrolyte to extract oxygen gas from water, thereby directly analyzing the oxygen isotope $^{17}O$ as oxygen gas form.

Preferably, in the isotope ratio mass spectrometric determination for stable isotopic composition of water according to the present invention, the electrolysis is conducted by using an electrolysis cell which is contacted with a PEM which is made of fluorocarbon polymer plated non-electrolytically with platinum, iridium or iridium-rhodium alloy, and which is sandwiched between a cathode and an anode both made of porous titanium plated with platinum. Then water is electrolyzed by introducing water into the anode side and supplying a DC current between the anode and the cathode.

BRIEF DESCRIPTION OF DRAWINGS

The nature, principle, and utility of the invention will become more apparent from the following detailed description when read in conjunction with the accompanying drawings in which like parts are designated by identical reference numbers, in which.

BEST MODE FOR CARRYING OUT THE INVENTION

In the following, embodiments of the present invention will be explained in detail with reference to the drawings.

Figure 1:
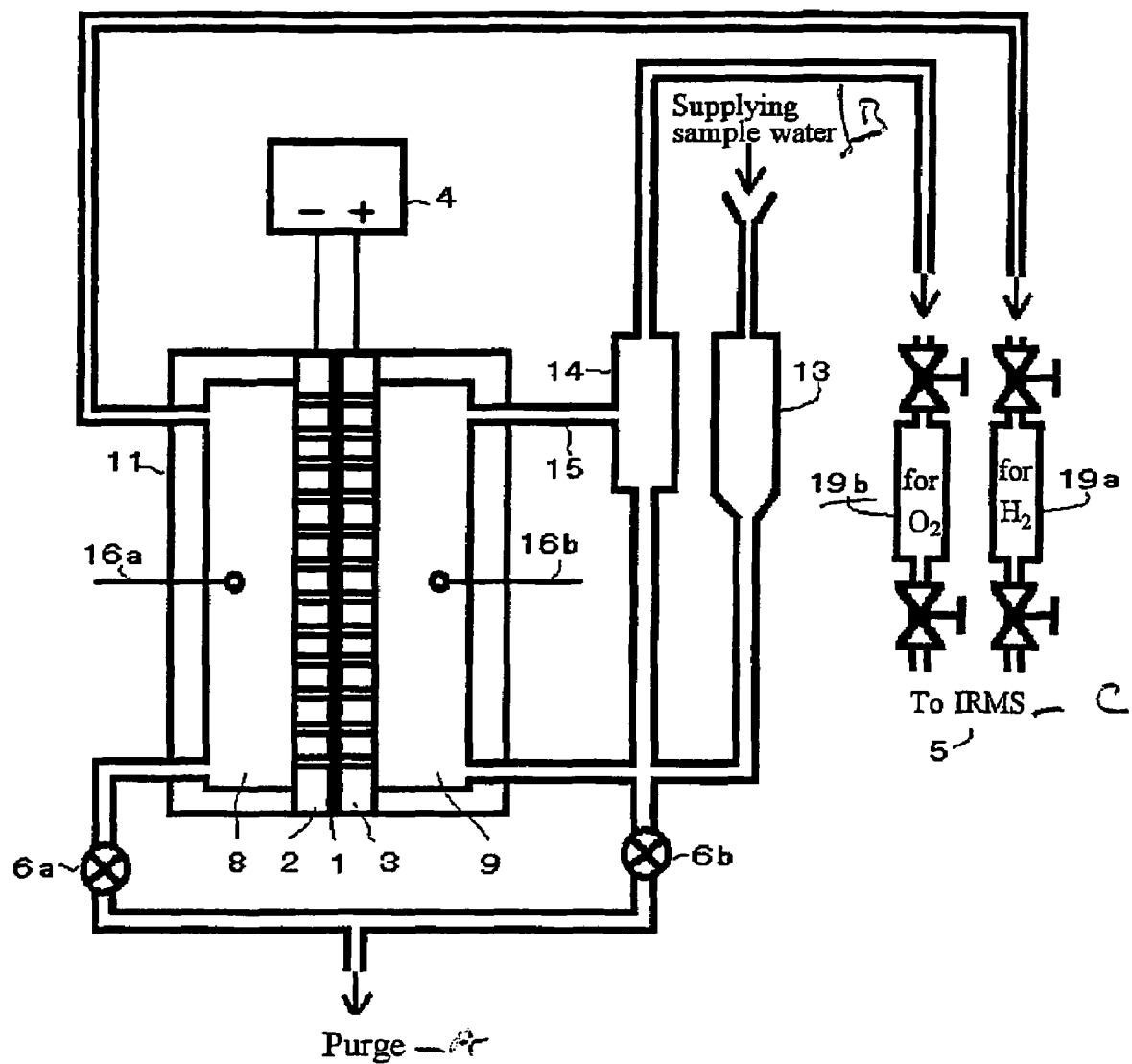
FIG. 1 is a block diagram showing a first embodiment of a WED for the determination of stable isotopic composition of water according to the present invention.

FIG. 1 is a block diagram of a first embodiment of a WED for the determination of stable isotopic composition of water according to the present invention. A WED for the determination of stable isotopic composition of water (20) according to the first embodiment of the present invention shown in FIG. 1 has a double-chamber type electrolysis cell (11) including a cathode chamber (8) and an anode chamber (9) in which a PEM (1) is sandwiched between a cathode (2) and an anode (3). The WED for the determination of stable isotopic composition of water (20) according to the first embodiment of the present invention is used in association with measurement of water isotope in an IRMS (5).

For the PEM (1), the one made of a fluorocarbon polymer material to which platinum is plated non-electrolytically is used. Iridium, rhodium or iridium-rhodium alloy is also suited for non-electrolytic plating besides platinum. The PEM which is made of fluorocarbon polymer plated non-electrolytically with platinum, iridium, rhodium or iridium-rhodium alloy used in the first embodiment of the present invention is much superior in the ability for gas barrier to general-purpose membranes. In addition, low contact resistance between the PEM and electrodes and low specific resistance of the PEM provide high electrolysis efficiency.

Both the cathode (2) and the anode (3) are formed of porous titanium plated with platinum. The cathode (2) and the anode (3) are connected with a DC power supply (4).

Sample water is first introduced to a sample water container (13) and then introduced to the anode chamber (9). Examples of the sample water include melted polar ice, rainwater, groundwater, and the like.

The sample water is continuously supplied to the anode chamber (9). The sample water is not supplied to the cathode chamber (8). This aims at improving the purity of hydrogen gas to be generated. The sample water introduced into the anode chamber (9) is then electrolyzed by supplying a DC current between the cathode and the anode. As a result of the electrolysis, oxygen gas is generated on the surface of the anode (3) placed in the anode chamber (9).

On the other hand, on the surface of a cathode (2), hydrogen gas is generated. Protons generated at the anode passed through the PEM (1), and at the cathode side, hydrogen gas is generated by bonding these protons under the presence of platinum catalyst plated on the PEM. Oxygen gas generated at the anode doesn't pass though the PEM because of its high ability for gas barrier. Hydrogen gas, generated at the cathode, also doesn't pass through the PEM because of its high ability for gas barrier.

Although water is introduced only to the anode chamber (9), a part of water vapor is permeated to the cathode side.

By the way, in the isotope ratio mass spectrometry, a correction should be made according to the temperature of sample water because stable isotopic composition of hydrogen gas and oxygen gas generated by electrolysis vary depending on the temperature. This is because isotope fractionation of hydrogen and oxygen during electrolysis depends on water temperature. In order to acquire temperature data required for such a correction, thermocouple gauges (16a), (16b) are provided for the cathode chamber (8) and additionally for the anode chamber (9).

Figure 2:
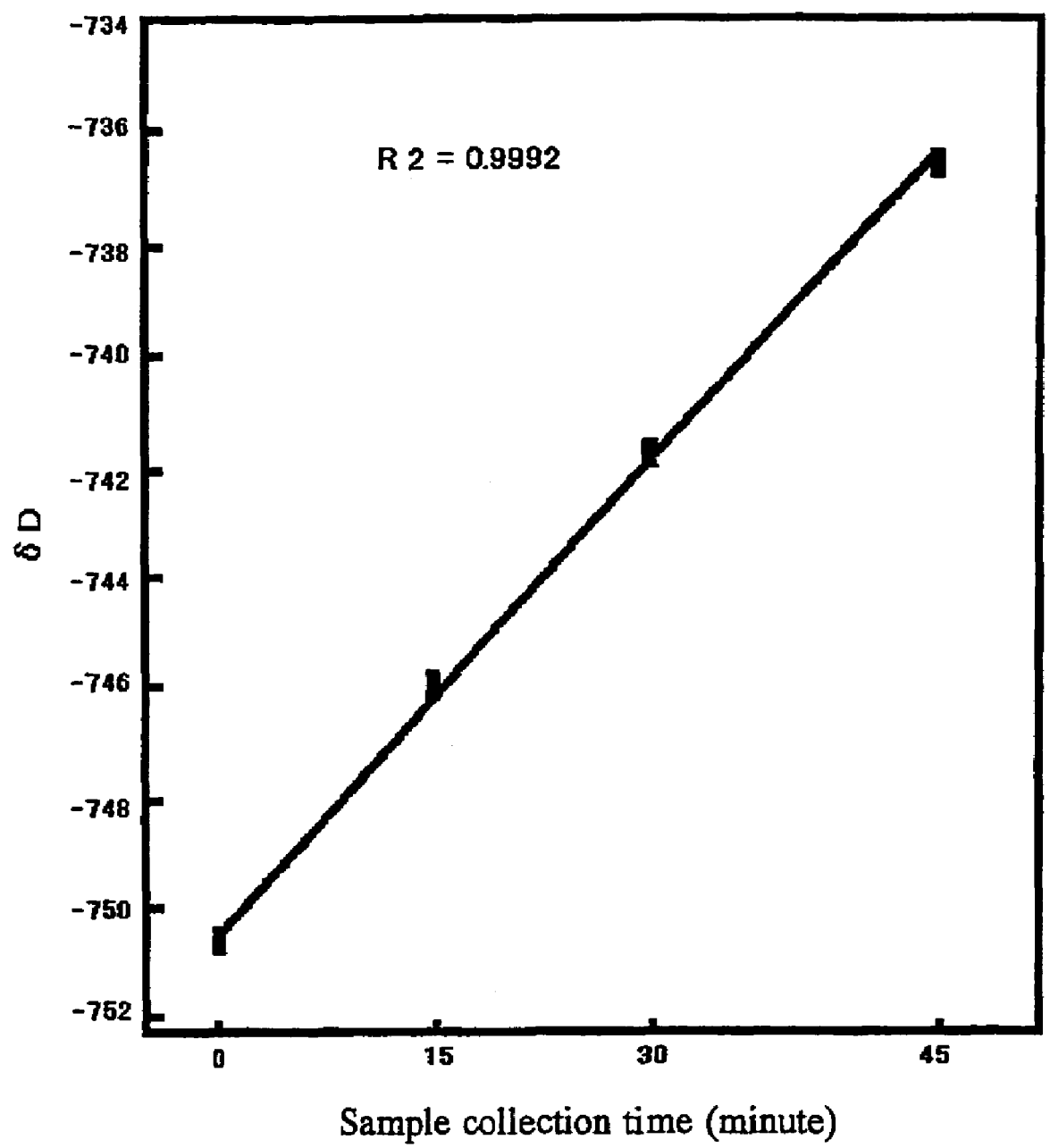
FIG. 2 is a characteristic chart showing hydrogen stable isotopic composition depending on the collection time.

In order to examine the relationship between the temperature of sample water and the stable isotopic composition of hydrogen and oxygen gases, the sample water of No. 1 was continuously electrolyzed according to the first embodiment of the WED for the determination of stable isotopic composition of water, the generated hydrogen gas was sampled four times every 15 minutes, and the hydrogen isotopic composition of this hydrogen gas was determined by IRMS. FIG. 2 shows results of the time series of hydrogen stable isotopic composition from identical water sample No. 1. In this figure, "δD" represents a value calculated from the definition 1. To be more specific, "δD" is a value obtained by subtracting an isotope ratio of $^2H$ (deuterium) to $^1H$ in a standard substance from that in a sample water, dividing this deviation by an isotope ratio in a standard substance, and then multiplying this ratio by 1000. It can be seen from FIG. 2 that the isotopic composition increases linearly with time of electrolysis. Therefore, in the measurement of hydrogen stable isotopic composition, capability of monitoring the temperature of sample water will provide a great merit in making a correction to the measurement result.

$$\delta D = \frac{2_{H(D)}/1_{H(samplewater)} - 2_{H(D)}/1_{H(standard\ substance)}}{2_{H(D)}/1_{H(standard\ substance)}} \times 1000 \qquad \text{[Definition 1]}$$

The oxygen gas generated on the anode side flows together with the saturated vapor from sample water to a gas-liquid separation tank (14) which is connected to the anode chamber (9) via piping (15), where the oxygen gas is flown into a gas sampler (19b) via the piping (15). On the other hand, the hydrogen gas is directly flown into a gas sampler (19a) that is connected to the cathode chamber (8) via the piping (15). The oxygen gas and the hydrogen gas sampled in the gas samplers (19a), (19b) are then introduced into the IRMS (5). The vapor accumulated in the cathode chamber (8) or the water discharged from the gas-liquid separation tank (14) is drained via the piping (15) equipped with solenoid valves (6a), (6b).

Since the rate of the generated gas depends on its molecular weight, $^{16}O$ is electrolyzed faster than $^{18}O$ or $^{17}O$. Therefore, if the sample water is significantly reduced due to the electrolysis duration, $^{18}O$ or $^{17}O$ become concentrated in the residual water, leading the result that the oxygen isotopic composition in the gas generated in early stage differs from that in final stage of electrolysis. This is also same situation for hydrogen isotope. Lighter isotope, $^1H$, has a faster electrolysis rate, so that heavier isotope, $^2H$ become concentrated in the residual water, leading the result that the hydrogen isotopic composition in the gas generated in early stage differs from that in final stage of electrolysis. However, according to the present invention, only a small part of sample water is electrolyzed to extract oxygen gas and hydrogen gas, and the standard water substance and the sample water is obtained in a same manner. Therefore, the problem of isotope enrichment in sample water described above will offset each other. In addition, the time required for obtaining oxygen gas and hydrogen gas from sample water is as short as several minutes. Moreover, it is possible o extract oxygen gas and hydrogen gas from sample water simultaneously.

Figure 3:
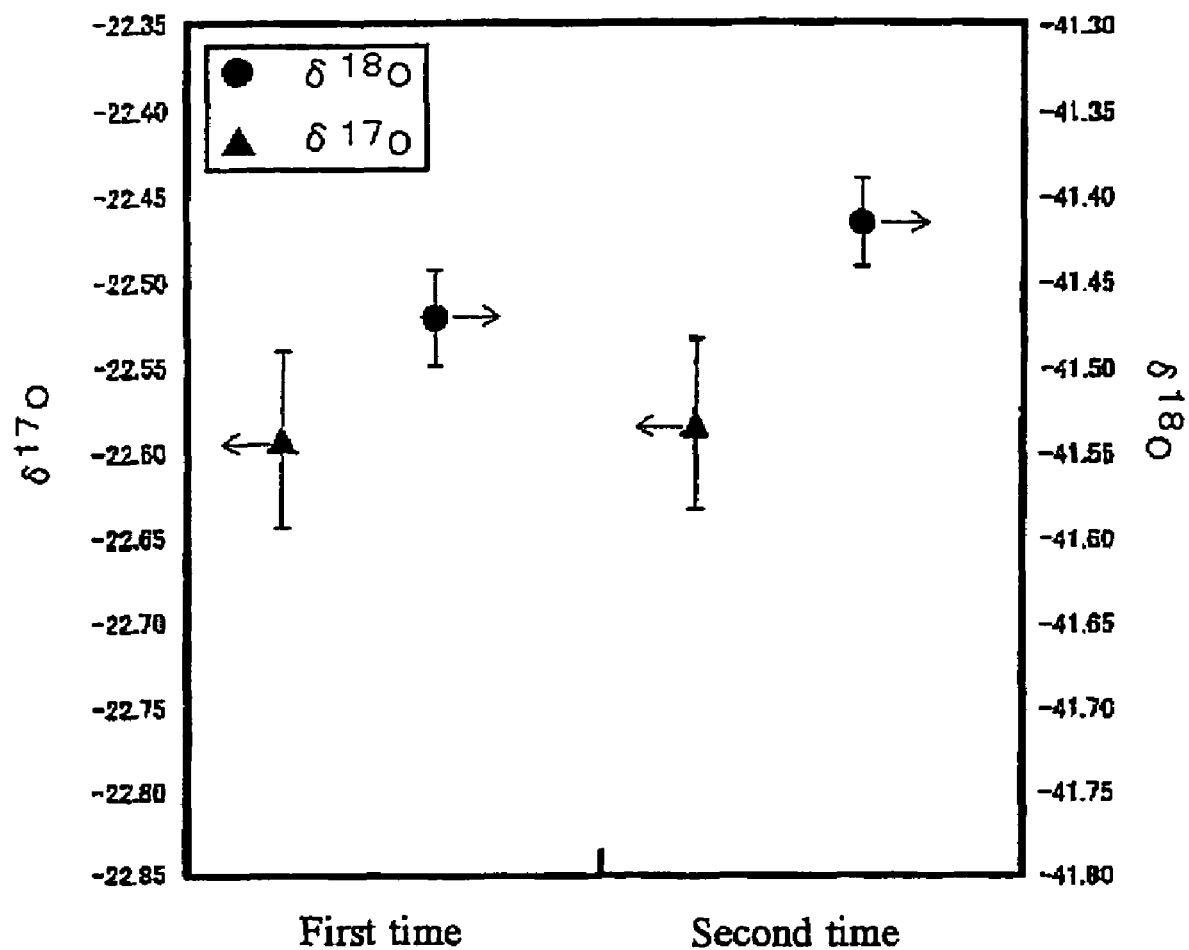
FIG. 3 is a characteristic chart showing oxygen stable isotopic composition of Sample No. 2.

Sample water of sample No. 2 was electrolyzed in the first embodiment of the WED for the determination of stable isotopic composition of water, and oxygen stable isotopic composition was determined by IRMS. FIG. 3 shows results of the oxygen stable isotopic composition of sample No. 2. In this figure, $\delta^{17}O$ is a value calculated by definition 2 and $\delta^{18}O$ is a value calculated by definition 3. Gas samples were collected in duplicate and introduced to IRMS. The error bar shows a range of analytical error by IRMS. As a result, it was found that analysis of $^{17}O$ is enabled by the present invention.

$$\delta^{17}O = \frac{^{17}O/^{16}O_{(samplewater)} - ^{17}O/^{16}O_{(standard\ substance)}}{^{17}O/^{16}O_{(standard\ substance)}} \times 1000 \quad \text{[Definition 2]}$$

$$\delta^{18}O = \frac{^{18}O/^{16}O_{(samplewater)} - ^{18}O/^{16}O_{(standard\ substance)}}{^{18}O/^{16}O_{(standard\ substance)}} \times 1000 \quad \text{[Definition 3]}$$

According to the first embodiment of the WED for the determination of stable isotopic composition of water, the sample water can be electrolyzed without adding any electrolyte that affects measurement of stable isotopic composition. Therefore, according to the present invention, it is possible to avoid various problems associated with mass spectrometry that are caused by adding an electrolyte such as copper sulfate.

According to the first embodiment of the WED for the determination of stable isotopic composition of water of the present invention, since a hydrogen gas and an oxygen gas can be extracted directly, rapidly and separately from sample water, it is possible to analyze a number of samples with ease, with safety, and at low cost in a very short time and achieve rapid analysis of $^{17}O$.

Figure 4:
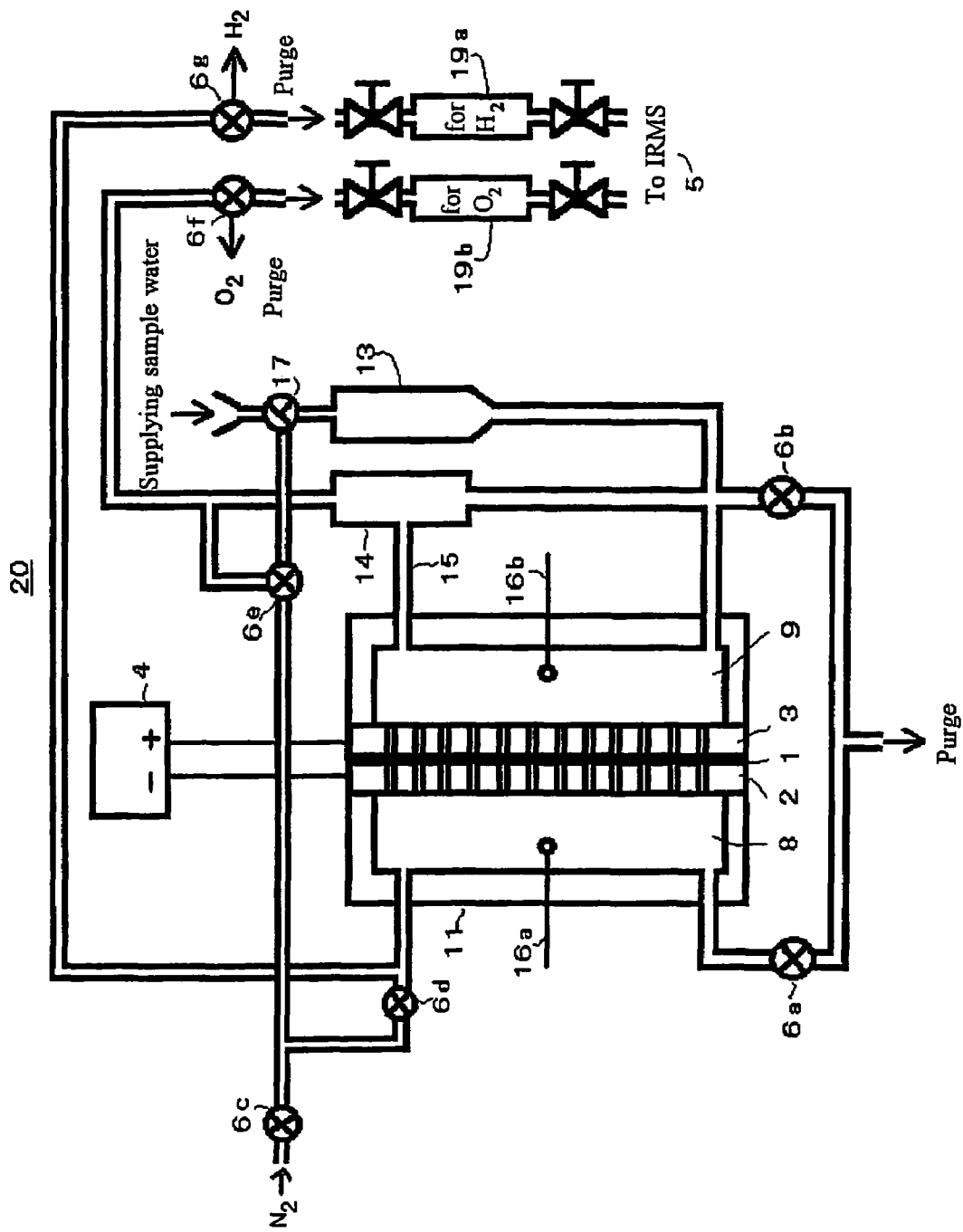
FIG. 4 is a block diagram showing a second embodiment of a WED for the determination of stable isotopic composition of water according to the present invention.

FIG. 4 is a block diagram of a second embodiment of a WED for the determination of stable isotopic composition of water according to the present invention. In the second embodiment of the WED for the determination of stable isotopic composition of water according to the present invention, the first embodiment of the electrolysis method for stable isotopic composition of water of the present invention as shown in FIG. 1 is further provided with nitrogen supply means. Nitrogen gas is supplied, via solenoid valves (6f), (6g) and a three-way stopcock (17), at three points: before sample water is introduced to the sample water container (13) via the piping (15) equipped with solenoid valves (6c), (6d), (6e); before oxygen gas is flown into the gas sampler (19b) from the liquid-gas separation tank (14); and before hydrogen gas is flown into the gas sampler (19a) from the cathode chamber (8). Whenever oxygen gas or hydrogen gas is flown into the IRMS (5), nitrogen gas is introduced so as to purge the atmospheric gas and water remaining in each pathway, in other words, in the piping (15).

Furthermore, the second embodiment of the WED for the determination of stable isotopic composition of water according to the present invention is so arranged that the generated gases are introduced into the piping (15) via the solenoid valves (6f), (6g). Valves of the gas samplers (19a), (19b) are closed except when conducting gas collection. In such situation, for preventing gas from continuing to flow into the piping (15) to increase the inside pressure and cause explosion, the solenoid valves (6f), (6g) act to let the gas inside the piping (15) escape to gas vent. By way of this action, it is possible to improve the safety. Furthermore, by letting gas flow into the piping (15) every time a test ends or a test starts, it is possible to avoid the contamination which occurs by mixing with previous gas. Therefore, reliability of analytical result of mass spectrometry is improved.

According to the second embodiment of the WED for the determination of stable isotopic composition of water of the present invention, more accurate determination becomes possible since the remaining gas and water vapor will not flow into the IRMS, and experimental failure are less likely to occur. Also an effect of improving the safety is achieved by preventing explosion.

Figure 5:
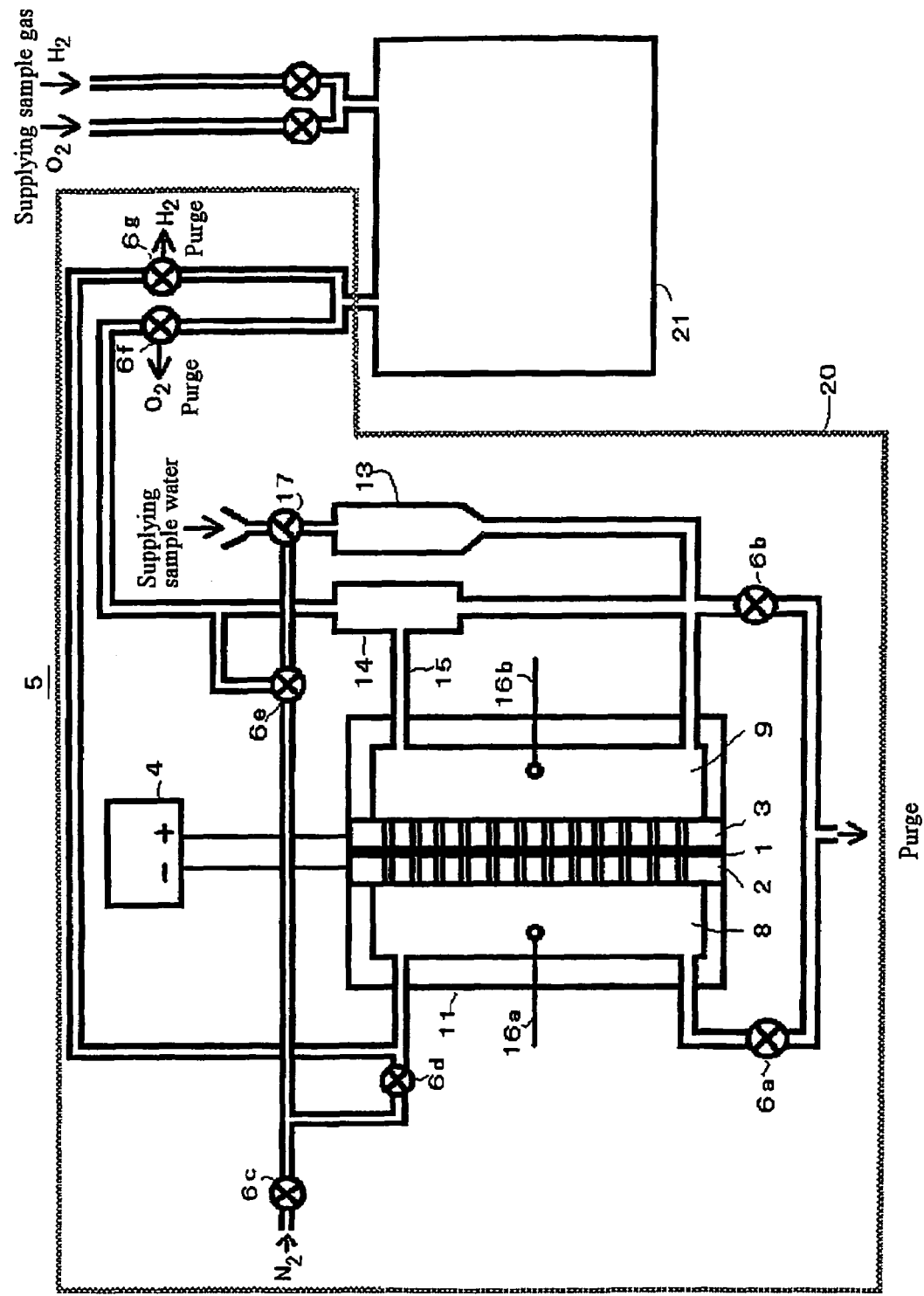
FIG. 5 is a block diagram showing the first embodiment of an IRMS in which a third embodiment of a WED for the determination of stable isotopic composition of water according to the present invention is incorporated.

FIG. 5 is a block diagram of the first embodiment of the IRMS in which a third embodiment of a WED for the determination of stable isotopic composition of water of the present invention is incorporated. The third embodiment of the WED for the determination of stable isotopic composition of water of the present invention is almost the same as the second embodiment of the WED for the determination of stable isotopic composition of water of the present invention shown in FIG. 4 except that it adopts on-line form in which oxygen gas and hydrogen gas generated by electrolysis are directly flown into the IRMS main unit (21) via the piping (15) rather than adopting the off-line form in which sampling into the gas samplers (19a), (19b) is conducted. The piping (15) is connected to the sample inlet of the IRMS main unit (21) so that only the gas to be determined is selected by means of valve operation. Oxygen gas and hydrogen gas generated by electrolysis continuously flow through the piping until they are subjected to mass spectrometry, so that they never contact with the ambient air. The IRMS main unit (21) is further provided with a dual-inlet with a standard gas inlet. To the standard gas inlet, oxygen gas or hydrogen gas which has known isotopic composition relative to the standard substance is selectively introduced as a working standard gas.

Figure 6:
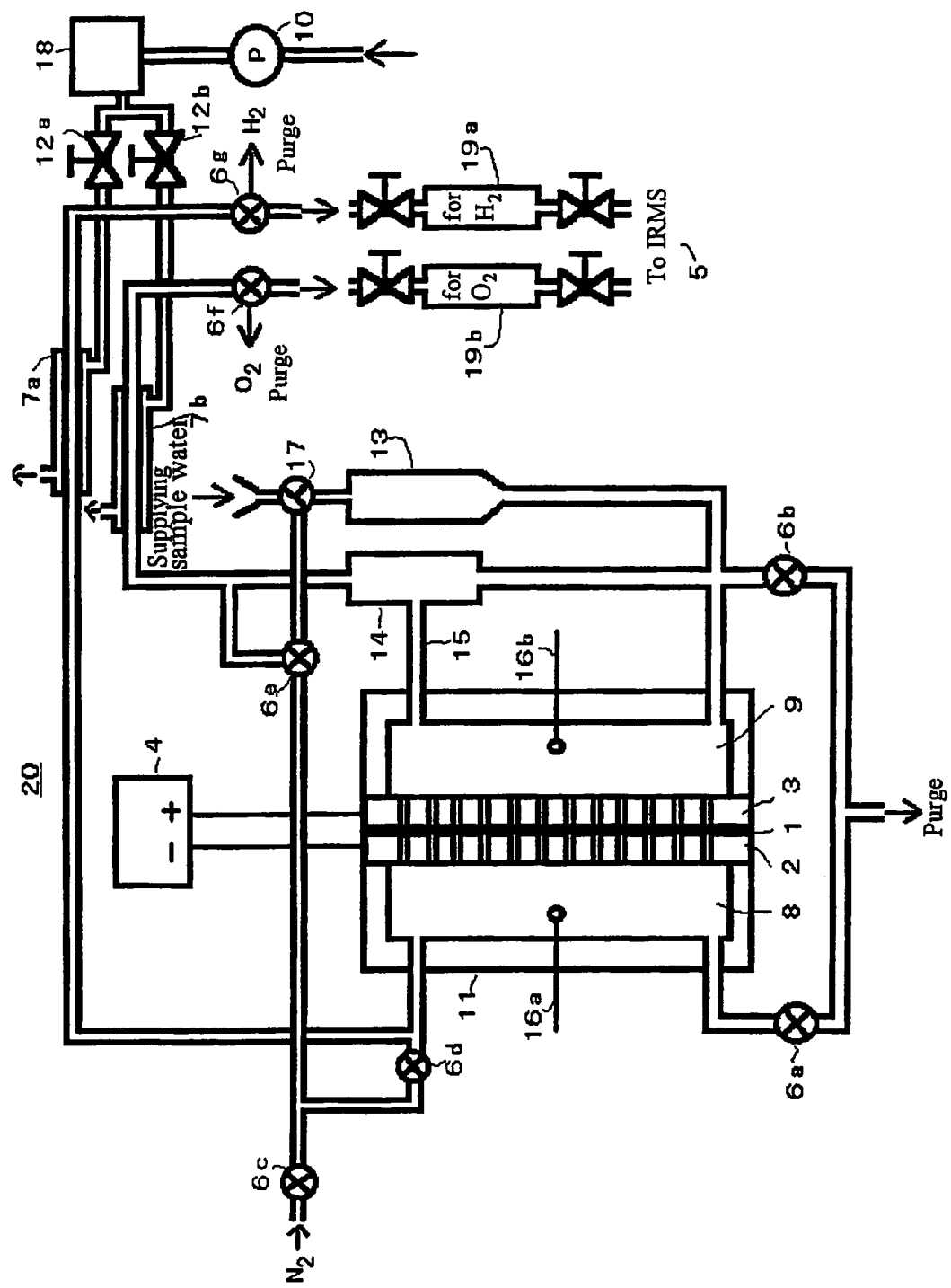
FIG. 6 is a block diagram showing a fourth embodiment of a WED for the determination of stable isotopic composition of water according to the present invention.

FIG. 6 is a block diagram of a fourth embodiment of a WED for the determination of stable isotopic composition of water of the present invention. In the fourth embodiment of the WED for the determination of stable isotopic composition of water of the present invention, the second embodiment of the WED for the determination of stable isotopic composition of water of the present invention is further provided with double tubes (7a), (7b). The double tubes (7a), (7b) are provided for dehumidification. The double tubes (7a), (7b) are connected to an air dryer (18) and provided with valves (12a), (12b) for controlling flow rate. The air dryer (18) supplied with air via a diaphragm pump (10) dries the air in its interior over silica gel to deliver it to the double tubes (7a), (7b). The tube walls of the double tubes (7a), (7b) are formed of vapor exchange membrane which is made of fluorocarbon polymers so that the air dried in the air dryer (18) is allowed to pass between the inner tube and the outer tube. The oxygen gas and hydrogen gas are dehumidified before being introduced into the IRMS (5) by removing only such moisture that inhibits determination, from the oxygen gas or hydrogen gas flown into the inner tube of the double tubes (7a), (7b). The expression "inhibit determination" is synonymous with "cause error in mass spectrometric determination of oxygen gas and hydrogen or cause failure of the IRMS".

According to the fourth embodiment of the WED for the determination of stable isotopic composition of water of the present invention, water vapor contained in the oxygen gas and hydrogen gas is also removed, providing the effects that the accuracy of determination by the IRMS is further improved and experimental failure are less likely to occur.

Figure 7:
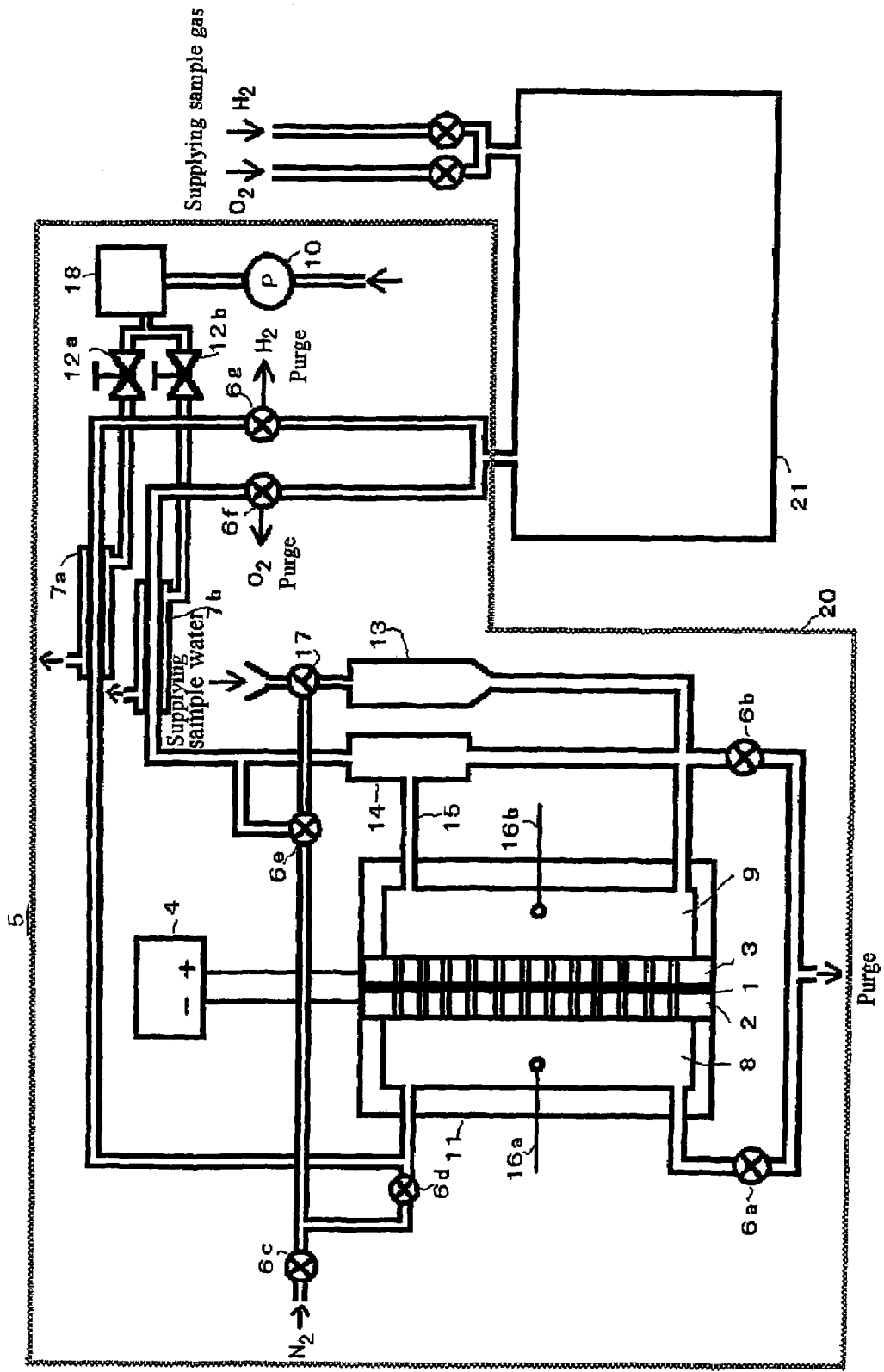
FIG. 7 is a block diagram showing the second embodiment of an IRMS in which a fifth embodiment of a WED for the determination of stable isotopic composition of water according to the present invention is incorporated.

FIG. 7 is a block diagram of the second embodiment of the IRMS in which a fifth embodiment of a WED for the determination of stable isotopic composition of water of the present invention is incorporated. The fifth embodiment of the WED for the determination of stable isotopic composition of water of the present invention is almost same as the fourth embodiment of the WED for the determination of stable isotopic composition of water as shown in FIG. 6, except that it adopts on-line form in which oxygen gas and hydrogen gas generated by electrolysis are directly flown into a IRMS main unit (21) via the piping (15) rather than adopting the off-line form in which sampling into the gas samplers (19a), (19b) is conducted. In this regard, the preset embodiment is the same as the second embodiment of the IRMS in which the third embodiment of a WED for the determination of stable isotopic composition of water of the present invention is incorporated.

The first embodiment of the water electrolysis method for the determination of stable isotopic composition of water includes: electrolyzing sample water without adding any electrolyte that affects the determination of stable isotopic composition; separately extracting hydrogen gas or oxygen gas and introducing them into an IRMS; and analyzing isotopes with regard to a hydrogen isotope or an oxygen isotope contained in the sample water. As the electrolysis cell in which electrolysis is conducted, any of single chamber type, dual chamber type, and triple chamber type is applicable insofar as it can separately extract hydrogen gas or oxygen gas without adding any electrolyte that affects the determination of stable isotopic composition. Particularly preferred is a dual chamber type electrolysis cell which includes a PEM which is made of fluorocarbon polymer plated non-electrolytically with platinum, iridium, rhodium or iridium-rhodium alloy, and a cathode and an anode made of porous titanium plated wit platinum and sandwiching the PEM, in which water is electrolyzed by introducing water into the anode side chamber and supplying a DC current between the anode and the cathode. In particular, the first embodiment of the WED for the determination of stable isotopic composition of water is more suitably used.

Oxygen stable isotopic composition in standard mean ocean water used as a standard substance is said to be $^{16}O:^{17}O:^{18}O=99.762:0.038:0.200$, and unlike $^{18}O$, the oxygen isotope $^{17}O$ in the form of compounds made up of oxygen and other atoms, such as water, carbon dioxide, and nitrous oxide, cannot be measured by using a IRMS due to existence of hydrogen isotope D, carbon isotope $^{13}C$ or nitrogen isotope $^{15}N$. In the case of nitrous oxide, $^{14}N^{15}N^{16}O$ having a molecular weight of 44.99809760 cannot be distinguished from $^{14}N_2{}^{17}O$ having a molecular weight of 45.0052790 by a present IRMS which has relatively low resolution to separate them. Moreover, difference is much smaller between $^{13}C^{16}O_2$ having a molecular weight of 44.9931840 and $^{12}C^{16}O^{17}O$ having a molecular weight of 44.9940456, and such difference cannot be measured even by using an high-performance IRMS which has a higher resolution than conventional IRMS (See, for example, Patent document 1).

In contrast to the above, the first embodiment of the water electrolysis method for the determination of stable isotopic composition of water enables direct analysis of oxygen isotope $^{17}O$ as a form of oxygen molecule, by electrolyzing sample water without adding any electrolyte which affects the determination of stable isotopic composition and extracting oxygen as a form of molecular oxygen gas. Direct determination of such oxygen isotope $^{17}O$ of water was conventionally impossible as a form of compounds such as water, carbon dioxide, or nitrous oxide because of the overlapping peaks of isotopes having the same mass number. According to the first embodiment of the water electrolysis method for the determination of stable isotopic composition of water, it is possible to separately extract oxygen gas and hydrogen gas by electrolysis of sample water and to introduce the oxygen gas directly to a conventional IRMS. The difference of mass between $^{17}O^{16}O$ (mass number 33) and $^{16}O^{16}O$ (mass number 32) can be detected by a conventional IRMS. It is possible to know the isotopic composition of $^{17}O$ in the sample water with high accuracy.

According to the water electrolysis method for the determination of stable isotopic composition of water, since hydrogen stable isotopes and oxygen stable isotopes can be directly and rapidly (in several minutes) extracted in the form of hydrogen gas (such as $^1H^2H$, $^1H^1H$) and oxygen gas (such as $^{16}O^{17}O$, $^{16}O^{18}O$, $^{16}O^{16}O$) from the sample water, it is possible to analyze a number of samples with ease, with safety and at low cost in a very short time, and realize rapid analysis of $^{17}O$.

The invention is not limited to the above embodiments and various modifications may be made without departing form the spirit and scope of the invention. Any improvement may be made in part or all of the components.

INDUSTRIAL APPLICABILITY

Since the WED for the determination of stable isotopic composition of water and the water electrolysis method for the determination of stable isotopic composition of water in the present invention are configured as described above, it is possible to analyze a number of samples with ease, with safety and at low cost in a very short time, and realize rapid analysis of $^{17}O$.

What is claimed is:

1. A water electrolysis device for determination of stable isotopic composition of water and performing mass spectrometry of one of hydrogen stable isotopic composition and oxygen stable isotopic composition, the water electrolysis device comprising a proton exchange membrane which is made of fluorocarbon polymer plated non-electrolytically with one of platinum, iridium, rhodium and iridium-rhodium alloy, and a cathode and an anode made of porous titanium plated with platinum and sandwiching the proton exchange membrane between them, wherein water is electrolyzed by introducing water into the anode side and supplying a DC current between the anode and the cathode, and oxygen gas generated at the anode and hydrogen gas generated at the cathode are respectively allowed to flow into an isotope ratio mass spectrometer.

2. The water electrolysis device according to claim 1, further comprising means for feeding nitrogen gas to each of a pathway which leads the oxygen gas generated at the anode to the isotope ratio mass spectrometer and a pathway which leads the hydrogen gas generated at the cathode to the isotope ratio mass spectrometer, whereby gas and water remaining in each pathway can be purged each time the oxygen gas or hydrogen gas is flown into the isotope ratio mass spectrometer.

3. The water electrolysis device for the determination of stable isotopic composition of water according to claim 1, further comprising a double-tube dehumidifying part in each of a pathway which leads the oxygen gas generated at the anode to the isotope ratio mass spectrometer and a pathway which leads the hydrogen gas generated at the cathode to the isotope ratio mass spectrometer, the double-tube dehumidifying part having an inner tube wall formed of a proton exchange membrane which is made of fluorocarbon polymer, wherein by letting air having dried with silica gel flow between an inner tube and an outer tube, only such water vapor which prevents mass spectrometric determination is removed from the oxygen gas or hydrogen gas flown into the inner tube, and thus the gases can be dehumidified before being introduced into the isotope ratio mass spectrometer.

4. A water electrolysis method of determining a stable isotopic composition of water for performing mass spectrometry of one of a hydrogen stable isotopic composition and an oxygen stable isotopic composition, the method comprising:

electrolyzing sample water without adding any electrolyte;

separately extracting hydrogen gas and oxygen gas to introduce them into an isotope ratio mass spectrometer; and conducting stable isotopic composition analysis of a hydrogen stable isotope and an oxygen stable isotope contained in the sample water.

5. The water electrolysis method for stable isotopic composition of water according to claim 4, wherein the electrolysis is conducted by using an electrolysis cell including a proton exchange membrane which is made of fluorocarbon polymer plated non-electrolytically with one of platinum, iridium, rhodium and iridium-rhodium alloy, and a cathode and an anode made of porous titanium plated with platinum and sandwiching the proton exchange membrane between them, in which water is electrolyzed by introducing water into an anode side chamber and supplying a DC current between the anode and the cathode.

6. A water electrolysis method of determining a stable isotopic composition of water, the method comprising:

electrolyzing sample water without adding any electrolyte to extract oxygen gas; and directly analyzing an oxygen isotope $^{17}O$ as a form of molecular oxygen electrolyzed from the sample water.

7. The water electrolysis method for stable isotopic composition of water according to claim 6, wherein the electrolysis is conducted by using an electrolysis cell including a proton exchange membrane which is made of fluorocarbon polymer plated non-electrolytically with one of platinum, iridium, rhodium and iridium-rhodium alloy, and a cathode and an anode made of porous titanium plated with platinum and sandwiching the proton exchange membrane between them, in which water is electrolyzed by introducing water into an anode side chamber and supplying a DC current between the anode and the cathode.

* * * * *